United States Patent [19]

Saffer

[11] 4,276,126

[45] Jun. 30, 1981

[54] SEPARATION OF ETHYLENE GLYCOL FROM N-METHYLPYRROLIDONE

[75] Inventor: Bernard A. Saffer, Cincinnati, Ohio

[73] Assignee: National Distillers and Chemical Corporation, New York, N.Y.

[21] Appl. No.: 99,342

[22] Filed: Nov. 30, 1979

[51] Int. Cl.$^3$ .............................................. B10D 3/36
[52] U.S. Cl. ...................................... 203/69; 203/70; 568/868
[58] Field of Search ............... 568/861, 862, 868, 871, 568/678, 852, 840; 203/68-70; 260/340.6, 340.9 R, 602

[56] References Cited

U.S. PATENT DOCUMENTS

| 3,074,962 | 1/1963 | Anderson | 203/69 |
| 3,809,724 | 5/1974 | Golden | 203/62 |
| 4,200,765 | 4/1980 | Goetz | 568/862 |

*Primary Examiner*—Frank Sever
*Attorney, Agent, or Firm*—Kenneth D. Tremain

[57] ABSTRACT

Mixtures containing ethylene glycol and N-methylpyrrolidone can be separated by azeotropic distillation by employing a $C_7$–$C_{10}$ hydrocarbon, having a boiling point between 110° and 190° C. as the azeotroping agent. An azeotrope of the hydrocarbon and ethylene glycol constitutes the overhead product while the bottoms product comprises N-methylpyrrolidone.

8 Claims, No Drawings

SEPARATION OF ETHYLENE GLYCOL FROM N-METHYLPYRROLIDONE

BACKGROUND OF THE INVENTION

1. Field of the Invention

This invention relates to the separation of closely boiling organic compounds. More particularly, this invention relates to the separation of ethylene glycol and N-methylpyrrolidone. This invention is especially concerned with recovering ethylene glycol as a product by means of azeotropic distillation from reaction mixtures employing N-methylpyrrolidone as a solvent.

In one method of producing ethylene glycol, disclosed in commonly assigned U.S. patent application Ser. No. 884,877, filed Mar. 9, 1978, synthesis gas is employed to convert formaldehyde to ethylene glycol in the presence of a rhodium catalyst. N-methylpyrrolidone is a preferred solvent in this process. Recovery of the N-methylpyrrolidone solvent for re-use and separation of pure ethylene glycol from the reaction mixture constitute important aspects in the commercial attractiveness of the overall process. However, the relative volatilities and the boiling points of the solvent and the desired product are so close that fractional distillation in commercial distillation equipment is impractical and uneconomical.

A process which would permit the effective and economic recovery of ethylene glycol from the N-methylpyrrolidone solvent is highly desirable.

2. Description of the Prior Art

Azeotropic distillation is a well known means of separating two different compounds or types of compounds having boiling points in close proximity. A third component which forms an azeotrope with one of the closely boiling components is added, the mixture is subjected to distillation and the azeotrope is removed as the overhead thereby effecting separation of the closely boiling components. This third component, called an azeotroping agent, is often separated subsequently from the component with which it forms the azeotrope by conventionally known means, such as decanting, and returned to the distillation apparatus for reuse. Each closely boiling binary system presents its own special problems so as to render past experience of little value and future results unpredictable. Thus, the selection of an azeotroping agent is seldom a simple task. Not only must the azeotroping agent form an azeotrope with the right volatility but the components of the azeotrope must be capable of being separated subsequently in highly pure form for either reuse in the process or recovery as a final saleable, useful product. In addition, the azeotroping agent should be relatively inexpensive, non-toxic, non-reactive and non-corrosive.

Ethylene glycol has been the subject of azeotropic distillation in the prior art. U.S. Pat. No. 2,218,234 discloses the use of toluene to form a three component azeotrope with ethylene glycol and water thereby effecting a separation of these components from a mixture occurring in the photographic industry which also contains salts, dyes and other contaminants. Aromatic hydrocarbons, other than benzene, i.e. toluene, ethyl benzene, etc., have been found in U.S. Pat. No. 3,074,962 to be effective in separating ethylene carbonate from ethylene glycol by forming an azeotrope with the glycol. In U.S. Pat. No. 3,809,724, mixtures of ethylene glycol and its lower carboxylate esters have been separated by employing as an azeotroping agent with the ethylene glycol, organic compounds having a boiling point between 135°–190° C. such as, acyclic and cyclic saturated hydrocarbons, alkyl-substituted benzenes and halogenated aromatic hydrocarbons. U.S. Pat. No. 4,021,311 is closely related to U.S. Pat. No. 3,809,724 and discloses that 1,2,3-trimethyl benzene is a particularly effective azeotroping agent in separating ethylene glycol from its carboxylate esters.

Ethylene glycol itself has found utility as an azeotroping agent. U.S. Pat. No. 3,392,090 discloses that ethylene glycol will form an azeotrope with less polar alkyl phenols to effect a separation from more polar alkyl phenols.

N-Methylpyrrolidone has been disclosed in U.S. Pat. No. 3,132,078 as forming an azeotrope with non-naphthalenic hydrocarbons to produce the overhead while naphthalenic hydrocarbons pass into the bottoms product.

The prior art provides few guidelines to the skilled artisan faced with the task of separating ethylene glycol from N-methylpyrrolidone. Both have functioned as azeotropic agents while ethylene glycol has been recovered as a part of an azeotrope from a variety of mixtures but not, so far as the prior art teaches, from a mixture comprising N-methylpyrrolidone.

It is thus among the objects of this invention to provide a means for effectively separating a mixture comprising ethylene glycol and N-methylpyrrolidone.

SUMMARY OF THE INVENTION

In accordance with the present invention, it has been found that ethylene glycol can be separated from N-methylpyrrolidone in an azeotropic distillation process by employing as the azeotroping agent a $C_7$–$C_{10}$ hydrocarbon having a boiling point between 110° and 190° C. More particularly, this invention is directed to a process for recovering ethylene glycol from a mixture comprising ethylene glycol and N-methylpyrrolidone which comprises:

(a) subjecting said mixture, together with an azeotroping agent of a $C_7$–$C_{10}$ hydrocarbon having a boiling point between 110° and 190° C., to azeotropic distillation in a distillation zone whereby an overhead product and a bottoms product are produced, said overhead product comprising an azeotrope of said azeotroping agent and said glycol and said bottoms product comprising said N-methylpyrrolidone, (b) separating said overhead product into a first phase comprising said azeotroping agent and a second phase comprising said glycol, (c) returning at least a portion of said first phase to said distillation zone as reflux and (d) recovering said glycol from said second phase.

The azeotropic distillation of this invention is conducted in conventionally available distillation equipment and under process conditions normally utilized in such processes. The temperatures employed are those one skilled in the art would find necessary to effect the desired separation at the column pressures encountered which can be atmospheric as well as superatmospheric and subatmospheric. The pressure employed is not critical and may well be dictated, as those skilled in the art can appreciate, by the pressures employed in processing equipment located upstream and/or downstream from the azeotropic distillation apparatus employed to practice the subject invention.

DESCRIPTION OF THE PREFERRED EMBODIMENTS

Broadly, it has been found that mixtures of ethylene glycol and N-methylpyrrolidone can be separated by azeotropic distillation when a $C_7$–$C_{10}$ hydrocarbon having a boiling point between 110° and 190° C. is added thereto to form an azeotrope of ethylene glycol plus the hydrocarbon which forms an overhead product. Upon settling, this azeotrope forms a two-phase liquid, one phase being essentially hydrocarbon while the other phase contains ethylene glycol plus some (usually less than 5%) hydrocarbon. One of the particularly novel features of the invention is the fact that no detectable amounts of N-methylpyrrolidone are found in the overhead vapor from this azeotropic distillation. This result was completely unexpected and constitutes one of the features of this process which makes it commercially attractive since it greatly simplifies the downstream processing of the overhead product. The N-methylpyrrolidone is recovered in the bottoms product and normally constitutes a major portion of the bottoms product.

The azeotroping agents which may usefully be employed in separating ethylene glycol from N-methylpyrrolidone are generally described as $C_7$–$C_{10}$ hydrocarbons having a boiling range between 110°–190° C., preferably 130°–170° C. These useful hydrocarbons include saturated hydrocarbons, both acyclic and cyclic. Aromatic hydrocarbons may also be employed and are, in fact, preferred with alkyl substituted benzenes being especially preferred.

Among the saturated acyclic hydrocarbons, heptanes, octanes, nonanes and decanes may be used while the cyclic saturated hydrocarbons include, for example cycloheptanes and trialkyl cyclohexanes and cycloheptanes. Useful aromatic hydrocarbons include toluene, the xylenes (o-m-p and mixtures thereof), cumene and such trialkyl benzenes as 1,2,4- and 1,3,5-trimethylbenzene.

The distillation equipment in which this invention may be practiced can be any conventional fractional distillation unit which includes a bubble-tray column or a packed bed column containing sufficient theoretical plates for the desired separation, usually 5 to 50 theoretical plates. The temperture employed will be dependent to some degree on the operating pressure and will, of course, vary with the azeotroping agent employed but generally reboiler temperatures of 120° to 215° C. are employed in this azeotropic distillation. In general, atmospheric pressure is employed in the settling drum associated with the overhead condenser but subatmospheric pressures may be employed, especially where the azeotropic distillation unit is located downstream or upstream from other processing equipment which must be maintained at a particular operating pressure, as those skilled in the art can appreciate.

The azeotrope recovered as an overhead product is condensed and passed to a settling drum where the liquid separates into two phases. The hydrocarbon phase containing a small quantity, if any, of ethylene glycol is returned in part to the tower top as reflux and in part further down the column. The glycol phase containing some hydrocarbon (less that 3 vol. %) is separated from the hydrocarbon phase, for example, by decanting. Following separation, the glycol phase can be treated to remove any hydrocarbon present so as to recover the glycol in the desired degree of purity. Fractional distillation is one of the conventional means that may be usefully employed to effect the desired ethylene glycol recovery but other known separation or treating processes may also be found to be useful. The bottoms product is essentially N-methylpyrrolidone which can be returned to an upstream processing unit to serve as a solvent in the production of additional quantities of ethylene glycol. Where necessary or desirable, this bottoms stream can be subjected to further processing where higher purity N-methylpyrrolidone is required.

The following examples will serve to further illustrate the process of the invention.

EXAMPLE 1

A 250 ml pot connected to a Podbielniak column was charged with 150 ml of toluene. After a short reflux period, a small fraction (BP 110° C.) was obtained at a high reflux ratio and labeled sample A. 50 ml of N-methyl-2-pyrrolidone (NMP) were added to the pot and after one hour total reflux, sample B was obtained at high reflux. 5 gms of ethylene glycol were then added to the pot and, after one hour total reflux period, a 13 ml fraction was removed as Sample C. This fraction separated into two phases, a top hydrocarbon phase and a bottom glycol phase. Each of the samples was analyzed by GLC with the following results:

| Sample | % Toluene | % Ethylene glycol | % NMP |
| --- | --- | --- | --- |
| A | 99.9 | — | — |
| B | 99.9 | — | 0 |
| C (top) | 99.7 | 0 | 0 |
| C (bottom) | 9.1 | 86.6 | 0 |

EXAMPLE 2

Example 1 was repeated using xylene (mixed isomers) instead of toluene with the following results:

| Sample | % Xylene | % Ethylene glycol | % NMP |
| --- | --- | --- | --- |
| B | 99.3 | — | 0 |
| C (top) | 99.6 | 0 | 0 |
| C (bottom) | 1.2 | 95.5 | 0 |

EXAMPLE 3

A 250 ml pot connected to a Podbielniak column was charged with 300 ml of o-xylene. After a small heads cut (10 ml) to remove impurities, 102 gm of a solution containing 4% water, 5% methanol, 7% ethylene glycol and 84% NMP were added. The volatiles (water and methanol) were removed first, then the glycol fraction was obtained as a 2 phase solution. Analysis of the glycol phase showed 89% ethylene glycol, 1.0% o-xylene, 10% water and 0% NMP.

EXAMPLE 4

A 50 plate Oldershaw column, fitted with a 2 liter pot was charged with 500 ml of cumene, 100 ml of NMP and 115 ml of ethylene glycol and approximately 80 ml of methanol. The volatiles were removed first, then the cumeneethylene glycol azeotrope distilled overheads at 114½° C. The overhead sample separated into two phases. Methanol was added to this two phase sample until a single phase was obtained. Analysis of this sample showed 16% ethylene glycol, 84% cumene and 0% NMP.

EXAMPLE 5

A 4-foot long, 1 inch diameter packed column was charged with 500 ml of 1,2,4 trimethylbenzene, 200 ml of NMP and 100 ml of ethylene glycol. The ethylene glycol-hydrocarbon azeotrope distilled overhead at 156° C. and, on cooling, separated into two phases which, when combined as in Example 4, contained 16% glycol.

EXAMPLE 6

Example 5 was repeated using n-octane as the hydrocarbon. The glycol azeotrope distilled overhead at 121° C. On cooling the distillate separated into two phases containing 3.8% glycol when combined as in Example 4.

EXAMPLE 7

Trimethylcyclohexane was prepared by reducing 473 grams of 1,2,4 trimethylbenzene with a catalyst of 5% ruthenium on carbon under mild conditions, viz., 1% catalyst, 500 psig $H_2$ and 100° C. GLC analysis indicated complete reduction of the aromatic. The trimethylcyclohexane produced had a boiling point of 141° C. (reported literature values: 135–136, 138–139 and 141°–143° C.). The catalyst was filtered off and 500 ml of the trimethylcyclohexane were charged to a distillation pot together with 200 ml of N-methylpyrrolidone and 100 ml of ethylene glycol and distilled in a 3'×1" ID packed column at a 3:1 reflux ratio. The overhead azeotrope boiled at 130° C. and separated into two phases. The lower or glycol phase was 5 vol. % of the total overhead and contained 97% glycol and 0% N-methylpyrrolidone. The upper phase was substantially all trimethylcyclohexane.

What is claimed is:

1. A process for recovering ethylene glycol from a mixture comprising ethylene glycol and N-methyl-pyrrolidone, said ethylene glycol being obtained by reacting $H_2$, CO and $H_2CO$ in the presence of rhodium catalyst and in N-methypyrrolidone as solvent, which comprises:
    (a) subjecting said mixture, together with an azeotroping agent of $C_7$–$C_{10}$ hydrocarbon having a boiling point between 110° and 190° C., to azeotropic distillation in a distillation zone whereby an overhead product and a bottoms product are produced, said overhead product comprising an azeotrope of said azeotroping agent and said glycol but containing no detectable amount of said methylpyrrolidone and said bottoms product comprising said N-methylpryrrolidone,
    (b) separating said overhead product into a first phase comprising said azeotroping agent and a second phase comprising said glycol,
    (c) returning at least a portion of said first phase to said distillation zone as reflux and,
    (d) recovering said glycol from said second phase.
2. A process according to claim 1 wherein said azeotroping agent is a $C_7$–$C_{10}$ hydrocarbon having a boiling point between 130° and 170° C.
3. A process according to claim 1 wherein said azeotroping agent is toluene.
4. A process according to claim 1 wherein said azeotroping agent is xylene.
5. A process according to claim 1 wherein said azeotroping agent is cumene.
6. A process according to claim 1 wherein said azeotroping agent is 1,2,4 trimethylbenzene.
7. A process according to claim 1 wherein said azeotroping agent is n-octane.
8. A process according to claim 1 wherein said azeotroping agent is 1,2,4 trimethylcyclohexane.